United States Patent [19]

Dalbow et al.

[11] 4,116,776

[45] Sep. 26, 1978

[54] DIAGNOSTIC BLOOD TEST AND KIT FOR DETECTING HUMAN CHORIONIC GONADOTROPIN

[75] Inventors: Milton H. Dalbow, Springdale; Hernan F. Acevedo, Allison Park; Malcolm Slifkin, Pittsburgh, all of Pa.

[73] Assignee: International Radioimmune Systems, Inc., Brighton, Mich.

[21] Appl. No.: 679,251

[22] Filed: Apr. 19, 1976

[51] Int. Cl.[2] .......................................... G01N 31/14
[52] U.S. Cl. ........................ 195/103.7; 195/103.5 R; 195/99
[58] Field of Search ................ 195/103.5 R, 99, 103.7

[56] References Cited

U.S. PATENT DOCUMENTS 3,791,932  2/1974  Schuurs et al. ............... 195/103.5 R

OTHER PUBLICATIONS

Clinical Chemistry, vol. 17, No. 7, p. 651, (1971).

Primary Examiner—Alvin E. Tanenholtz
Attorney, Agent, or Firm—Cullen, Sloman, Cantor, Grauer, Scott & Rutherford

[57] ABSTRACT

Malignant neoplastic cells synthesize and secrete human chorionic gonadotropin into the circulatory system, where the glycoprotein hormone is collected or adsorbed by the host's lymphocytes. This application discloses a clinical diagnostic test and kit for determining the presence of human chorionic gonadotropin in blood. Where the test is positive in a man or a non-pregnant woman cancer is present in the host.

19 Claims, 3 Drawing Figures

DIAGNOSTIC BLOOD TEST AND KIT FOR DETECTING HUMAN CHORIONIC GONADOTROPIN

FIELD OF THE INVENTION

Generally, the present invention relates to diagnostic procedures and clinical test kits for determining the presence or absence of the human chorionic gonadotropin hormone in blood and thereby the presence of cancer.

The reason why a mother is able to accept her fetus as an allographt when a large percentage of the potential antigenic sites of the fetus are different from those of the mother, has long been a mystery. It is known that the fetal trophoblast engrafts itself on the maternal endometrium while exposed to immunocompetent maternal lymphocytes. It has now been suggested that human chorionic gonadotropin is a trophoblastic surface antigen which blocks the action of the maternal lymphocytes, Adcock, et al, Science, Vo. 171,845–847 (1973).

Human chorionic gonadotropin (hCG) has been detected very early in gestation (7 days) and is now used as a diagnostic test for pregnancy. As stated, this hormone is a glycoprotein and, like other glycoprotein hormones including follicle-stimulating hormones (hFSH), luteinizing hormone (hLH) and thyrotropin, it consists of two non-covalently linked subunits, including alpha and beta. In contrast to the alpha-subunits, the amino acid composition of the beta subunit of the hCG differs substantially from the other glycoproteins.

The larger beta-subunit of hCG is the hormone-specific unit. Human chorionic gonadotropin is a sialoglycoprotein hormone, wherein 80 percent of the terminal groups of the beta-subunit are sialic acid residues (N-acetyl-neuraminic acid). The chemical structure of human chorionic gonadotropin and the beta-subunit is set forth in more detail in Sairam, et al, Biochimica et Biophysica Acta; 412,70–81 (1975).

Although the prior art has recognized that certain malignant neoplastic cells or tumors contain hCG, the correlation between hCG and cancer has been inconclusive or equivocal. It has now been determined that all cancer cells synthsize hCG by the highly specific and sensitive double-antibody test disclosed in our co-pending application for United States Patent. Further, it has now been determined by the present diagnostic test that hCG is collected or adsorbed by the lymphocytes of the host's circulatory system.

Similarly, the prior art serum tests for hCG of patients with known malignant tumors have been inconclusive. For example, in one recent study 40% of all men with malignant tumors tested positive for hCG, although up to 90 percent of the tests were positive among ovarian and testicular tumors, Barber et al, J. St. Barnabas Med. Ctr., Symposium August 1975. In the present radioimmunoassay for hCG, the serum is tested utilizing the double-antibody procedure developed by Vaitukaitis, et al, supra. Briefly, this test is as follows. Blood serum is added to a vial containing rabbit anti-beta hCG. Human chorionic gonadotropin radiolabeled with 125 I is then added and permitted to come to equilibrium. A portion of the radioiodine labeled hCG will then bind with the excess anti-beta hCG. Sheep anti-rabbit gamma globulin is then added to the vial to saturation. The anti-rabbit gamma globulin will then bind to the rabbit anti-beta hCG which will precipilate and can be separated by centrifugation. The supernatant is then removed and the radioactivity of the precipitate is counted and compared against a standard curve to determine the titer of hCG in the original serum sample.

At best, the sensitivity of the double-antibody radioimmunoassay is 5 to 8 mIU per ml, which is insufficient to detect many cancers. Further, it has now been discovered by the diagnostic test of this invention that human chorionic gonadotropin is concentrated in the lymphocytes, which are not even present in the serum test. It is therefore the purpose of the present diagnostic procedure to provide a highly specific sensitive test for the presence of hCG on lymphocytes, which has not been possible using the procedures disclosed in the prior art.

SUMMARY OF THE INVENTION

It has now been determined that the host's lymphocytes collect and bind the human chorionic gonadotropin hormone secreted by malignant neoplastic cells using the diagnostic test of this invention. Therefore, the prior art radioimmunoassay serum test has been examining the wrong fraction of the blood. Further, the sialic acid residues of hCG inhibit or block the antigenic sites on the beta hCG molecule that is bound to the lymphocytes, thus resulting in negative tests for hCG using the present double-antibody techniques. THerefore, the first step in the present diagnostic procedure is to strip the sialic acid residues from the beta hCG molecules, permitting binding of the antibody.

Briefly, the diagnostic test of the present invention includes separating the white blood cells from the whole blood to be tested. The lymphocytes comprise about 90 percent of the white blood cells thus separated. The lymphocytes, after rinsing, etc. are treated with a neuraminidase, to strip the sialic acid residues from the beta-subunit of hCG, permitting binding of the antibody to the glycoprotein. After washing, the cells are treated with an antiserum specific to the beta-subunit of human chorionic gonadotropin which includes a clinically detectable label. The label, which may be fluorescein, radioiodine or tritium, may be conjugated directly to the anti-beta hCG or the label may be conjugated to a second antibody. Finally, the lymphocyte cells are examined for the presence of the label. Where the label is radioactive, the concentration of hCG may be determined by measuring the radioactivity.

The diagnostic test and procedure of this invention thus eliminates the problems of the prior art, eliminating false positive tests and providing a positive test for human chorionic gonadotropin. Further, the test is far more sensitive than the radioimmunoassay tests of the prior art and provides a positive test for cancer.

DETAILED DESCRIPTION

Figure 1:
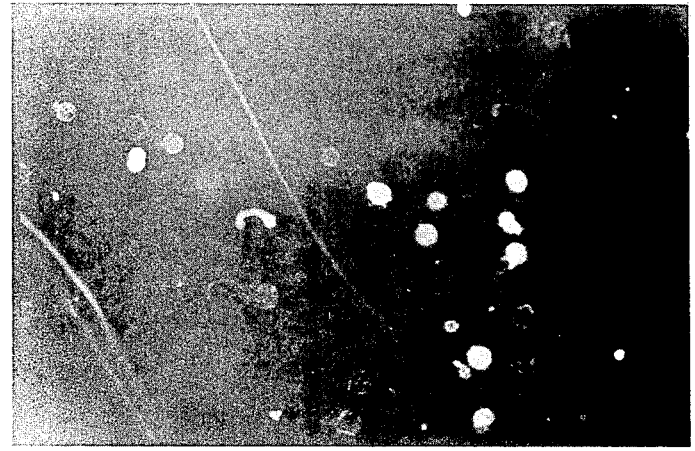

As described, the immunosuppresent action of human chorionic gonadotropin on the host's lymphocytes has been recognized by certain investigators using indirect parameters. No direct quantitative or qualitative technique for measuring hCG on lymphocytes has however been proposed. Instead, the prior art radioimmunoassay and other techniques measure the hCG concentration in the patients serum and attempt to correlate the hCG titer with other conditions of the host, such as pregnancy, trophoblastic diease or other cancers. Further, as described in our copending application, it has now been determined that all malignant neoplastic cells synthesize hCG, proving that human chorionic gonadotropin is the common denominator of all cells characterized as cancer.

The precise mechanism by which hCG protects the syncytiotrophoblast or neoplastic cell from the host's immunoprotective system is not fully understood, however it can now be said that malignant neoplastic cells synthesize hCG, which is localized in the plasma membrane of non-invasive cells, such as the HeLa cell, and hCG is concentrated in dense zones throughout the cell in highly tumorigenic cells. Further, hCG has now been found by the diagnostic procedure of the present invention bound to the host's lymphocyte cells. It is therefore believed that cancer cells secrete hCG as a part of the immunosuppresive action of hCG on the host's immune mechanism. This fact has now been further confirmed by comparing tests for the T-cell concentration by the E-Rossette technique with the lymphocyte-hCG test of this invention as described below.

It is further believed that malignant neoplastic cells secrete hCG very early in their generation, as evidenced by the complete correlation between hCG found in the host's lymphocytes and known cancer patients. Therefore, the diagnostic blood or lymphocyte test of the present invention provides a positive clinical test for cancer. In view of the sensitivity of the present tests, early detection of cancer is now possible, improving the chances of remission or cure by present techniques.

It is believed that the failure of the prior art to detect cancer in many cases was due to two factors; (1) the prior art was testing the wrong fraction of the blood, i.e. serum, and (2) the prior art technique is not sufficiently sensitive. Using the prior double-antibody technique, the antiserum specific for the beta-subunit of hCG does not bind with the hCG on the lymphocyte cells, resulting in false negative tests. This antiserum does however bind with the hCG associated with neoplastic cells. Therefore the binding mechanism between hCG and lymphocytes must be different from the binding mechanism between hCG and neoplastic cells. In view of the success of the present procedure, it is believed that sialic acid residues block or interfere with the antigenic sites of the beta hCG molecule. Therefore, it is necessary to strip or remove at least some of these sialic acid residues to provide receptors for the antiserum. This is accomplished in the procedure of the present invention by treating the lymphocyte cells with a neuraminidase, such as vibro cholerera neuraminidase (VCN) which is a sialic enzyme that attacks or strips the sialic acid residues from the beta hCG molecule, exposing the chemical binding sites for the antiserum used in the diagnostic procedure. VCN is commerically available from various souces, including Grand Island Biologicals Co., Grand Island, N.Y. Other neuraminidases may also be used in this procedure, such as clostridium neuraminidase. Following treatment with the neuraminidase, the antiserum specific to the beta-subunit of hCG will bind to the hCG molecules bound to the lymphocytes, permitting the present test for human chorionic gonadotropin.

Using the highly specific and sensitive lymphocyte-hCG diagnostic test of the present invention, cancer has been confirmed in patients having a wide variety of cancers, including cancers of the lung, breast, bladder, endometrium, ovary, and cervix. Further, quantitative correlations between the concentration of hCG and the stage of the cancer has also been found. Two types of controls have been utilized in the present tests. First, blood from known healthy patients test negative proving that the present test will not result in false positive tests. Second, labeled antiserum which is not specific to human chorionic gonadotropin may be used which also results in negative tests. Where the double-antibody technique is used, a non-specific second antibody may also be utilized.

The constituents of the diagnostic test kit are then as follows; (1) a neuraminidase, such as vibro cholerera neuraminidase (VCN) and (2) an antiserum specific to the beta-subunit of human chorionic gonadotropin, including a clinically detectable label such as radioiodine or tritium. The label may be conjugated directly to the anti-beta hCG or a second antiserum as described below. Where the double-antibody technique is utilized, the diagnostic test kit will also include the second antiserum which includes the clinically detectable label. Antiserum specific to the beta-subunit of human chorionic gonadotropin is available commercially from various sources, including International Radioimmune Systems, Inc., Howell, Michigan, Serono Laboratories, Inc., Boston, Mass., etc.

Briefly, the antiserum specific to the beta-subunit of hCG is produced as follows. Human chorionic gonadotropin is first obtained from human placenta and purified. The beta-subunit is separated and purified as described by others; Vaitukaitis et al, J. Clin. Endocrinol. 33:98 (1971). The purified beta-subunit of hCG is then serially injected into a host animal, commonly rabbits, raising the antibody in the host animal. The animal is then bled and the antiserum is extracted and purified as described in Naughton et al, Cancer Research, Vol. 35 p 1887 (1975).

Where the double-antibody technique is used, the second antiserum must be specific to the first antiserum. For example, where the first host animal is a rabbit, anti-rabbit gamma globulin is used. For example, rabbit immunogamma globulin G (IgG) is injected into a second host animal, such as a sheep or goat. The second host animal is then bled and the anti-rabbit gamma globulin is extracted, purified and labeled by conjugation to the preferred label. Methods of conjugating fluorescein and radioiodine to anti-rabbit gamma globulin are described in Methods In Enzymology, Watkins, Academic Press (1975). The diagnostic procedure is then as follows.

First, the lymphocytes must be separated from the whole blood to be tested. Normally, whole blood is collected in acid citrate dextrose (ACD). The white blood cells are then separated from the whole blood by the Boyum technique using ficol hypaque (F-H). In the Boyum technique, the whole blood is carefuly layered on top of the F-H and centrifuged to separate the blood into layers. The white blood cells may then be drawn off using a conventional Pasteur Pipette. Approximately 90 percent of the white blood cells are lymphocyte cells, the remaining cells including monocytes, neutrophils, etc. Although the diagnostic procedure of this invention is specifically concerned with the lymphocyte cells, it is not necessary to separate the lymphocytes from the remaining white blood cells.

The lymphocyte cells are then washed with phosphate buffered saline (PBS) pH 7.0, 0.01M and separated in a centrifuge. The lymphocyte cells are then treated with a neuraminidase, such as vibro cholerera neuraminidase (VCN). The neuraminidase is added to the lymphocytes, approximately ten units per $10^6$ cells. The purpose of VCN is to remove or strip the sialic acid residues which would interfere with the antigenic sites on the beta hCG molecules as described above. The cells should then be washed twice with PBS to remove excess VCN and centrifuged. The lymphocyte cells are now ready for hCG determination. Two procedures will now be described.

Where a radioactive isotope is utilized as the label, such as radioiodine 125, radioiodine 131 or tritium, the cells are tested in a test tube or vial. Where a single antibody is utilized, antiserum specific to the beta-subunit of hCG conjugated to a radioisotope is added. The cells are then washed with a suitable buffer, such as PBS, centrigued and rinsed. The radioactivity of the precipitate is then measured. Where the radioactive isotope is radioiodine 125 or 131, a gamma counter is used. Where the radioactive isotope is tritium, a beta counter is used.

As stated, the test will normally be run with a control, such as a non specific antiserum conjugated to the same radioactive isotope. Where the radiation is greater than the control, human chorionic gonadotropin is present in the lymphocyte cells tested and cancer is confirmed.

Where the double-antibody technique is utilized, the second antibody is specific to the first antibody and the radioactive isotope label is conjugated to the second antibody. For example, where rabbit anti-beta hCG is utilized as the first antibody, the second antibody would be anti-rabbit gamma globulin, which may be raised in a sheep or a goat as described. Briefly, the procedure for the double-antibody technique is then as follows. First, add one or two drops of appropriately diluted antiserum specific to the beta-subunit of hCG. As described, it is preferable to simultaneously run a negative control on a second sample of the lymphocytes with a non-specific antiserum, such as rabbit anti-horse serum. The samples are then incubated in a moist ambiant temperature for about 30 minutes. Gently rinse the excess antisera with PBS using a pipette. Then, wash the slides with PBS for 10 minutes with gentle agitation and centrifuge. Then, add one or two drops of labeled anti-rabbit gamma globulin, being careful to completely cover the cells. The radioactivity of the sample is then checked as described above.

Where fluorescein is used as a label, the same procedure is used except that the cells are tested on clear sides. Briefly, the procedure is then as follows. Place the slides on a flat, horizontal surface, preferably in a moist ambient temperature chamber, and apply one or two drops (0.05 ml) of appropriately diluted antiserum specific to the beta-subunit of hCG. Here again it is preferable to simultaneously run a ngeative control as described above. The slides are then incubated in a moist ambiant temperature for about 30 minutes. Then, gently rinse the excess antisera from the slides with PBS using a pipette. Then, wash the slides in PBS for 10 minutes with gentle agitation, using Coplin jars or a large volume staining dish. Drain the slides briefly and blot the excess fluid from around the cells. Do not permit the cells to dry. Where a single antiserum is used, the antiserum is conjugated to fluorscein and the cells are now ready for examination.

Where the double-antibody technique is utilized, the second antibody is conjugated to fluorescein as described. Following treatment with the first antiserum, place the slides on a flat horizontal surface in the moist ambiant temperature chamber and add one drop of reconstituted fluorescein-labeled anti-rabbit gamma globulin. As stated, care must be taken to completely cover the cells. The slides are then incubated again for 30 minutes in the moist ambiant temperature chamber. Then, the slides are rinsed and washed in PBS as described.

In the indirect fluorescein-labeled tests, the slides should be covered by adding a drop of mounting media, preferably 95 percent glycerin in PBS and covered with a cover slip. Where fluorescein is used as the label, the slides are examined with an ultra-violet light microscope having proper filters to permit the 530 m$\mu$ light to pass through the tissue. The fluorescein stain, if present, will show as an apple-green fluorescence at the site of the beta hCG foci. Fluorescein as a label has the advantage that it is extremely visable under ultra-violet light and the site of the hCG concentration may be viewed directly. A somewhat quantitative analysis of the hCG concentration may be made with a spectofluorimeter. The radioactive isotope test is simplier to preform, especially using the single antiserum test and the concentration of hCG may be determined quantitatively.

As stated, the identification of human chorionic gonadotropin in the lymphocyte cells may be due to one of two sources. The patient may be pregnant or cancer is present in the patient's system. Where a positive test has been made, a female patient of gestational age should be checked for pregnancy. The concentration of hCG in both maternal blood and urine rises to a maximum during the first trimester of pregnancy and declines thereafter to a low level during the latter portion of pregnancy. Most pregnancy tests are based upon this peak concentration or titer of hCG in the serum or urine during the first trimester. The lymphocyte-hCG test of this invention may therefore be used as a very early and sensitive pregnancy test. Where pregnancy may be ruled out and the lymphocyte-hCG test of this invention is positive, diagnostic procedures for the location of cancer should be begun immediately.

The following figures illustrate positive tests using the indirect fluorescein-labeled antibody tests of this invention. It is understood that the fluorescein in the test is a bright apple-green which appears as a light spot in the following photographs. FIG. 1 is a photographic enlargement of a positive test using the diagnostic procedure of the present invention with a fluorescein-labeled antisera. As stated, each test is performed with a control, preferably a labeled antisera which is non-specific either to hCG or the first antisera, if the double antibody test is used. This control is important because certain cells will stain with fluorescein. These cells are presently believed to be "dead" cells. These false stains may however be easily differentiated from the lymphocyte cells having hCG as shown in the photograph of FIG. 1. The brightly stained cells (white-opaque in the photograph) are falsely stained cells, probably dead cells. The cells lightly stained, particularly around the periphery of the cells, are lymphocyte cells containing hCG; evidencing cancer in the patient's system.

Figure 2:
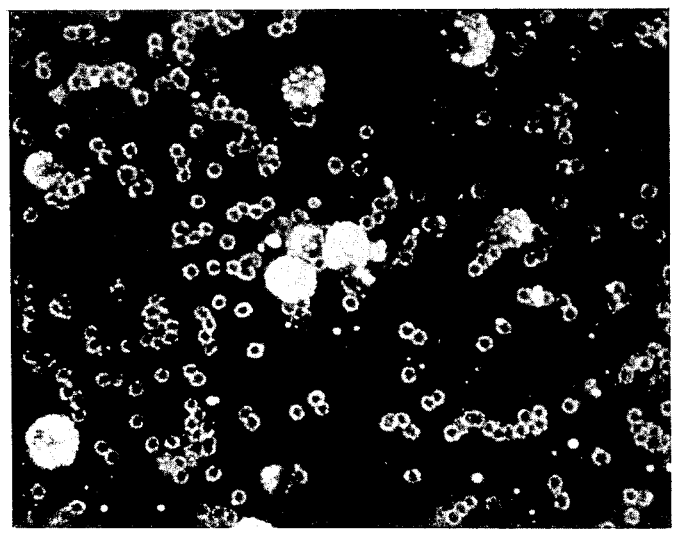

FIG. 2 is also a photographic enlargement of a positive test using a fluorescein-labeled antisera. In the photograph of FIG. 2, the "hob nail" effect is illustrated, wherein strongly positive cells (for hCG) have a series of bright spost around the periphery, resembling hob nails.

Figure 3:
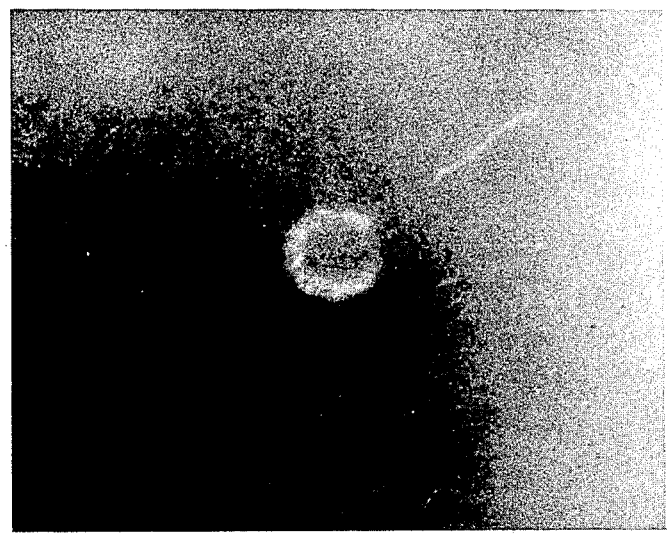

FIG. 3 is a photographic enlargement of a negative test for hCG using a fluorescein-labeled antisera and the diagnostic procedure of this invention. As shown, one cell is enlarged and appears as a phantom in the photograph. No evidence of fluorescein staining is found.

Table 1 lists the results of a series of test made on the lymphocytes of human cancer patients using the double-antibody technique labeled with fluorescein. All of the tests were positive on known cancer patients, as all of the controls were negative.

Table 1

| Type of Cancer | Stage of Cancer | No. of Patients | Mean % hCG Cells |
|---|---|---|---|
| Lung | — | 15 | 22.1 |
| Breast | — | 8 | 20.4 |
| Bladder | — | 3 | 23.0 |
| Endometrium | — | 2 | 23.0 |
| Ovary | — | 1 | 19 |
| Cervix | — | 1 | 15 |
| Lung | I | 1 | 15 |
| Lung | II | 3 | 9 |
| Lung | III | 5 | 19 |
| Lung | $IV_0$ | 2 | 27 |
| Lung | $IV_m$ | 4 | 35 |
| Breast | II | 3 | 11 |
| Breast | III | 4 | 26.5 |
| Breast | Metastasis | 1 | 25 |

It will be seen that there is a correlation between the stage of the cancer and the mean percent of lymphocyte cells found containing hCG. In the column of Stage of cancer, lung cancer has four stages. Little correlation was found between stage I and stage II with the few patients tested, however a definite correlation was found between the latter stages. $IV_0$ refers to stage four without metastasis, wherein 27 percent of the lymphocyte cells were found to have hCG. Where metastasis was found, $IV_m$, the percentage of cells having hCG was greater.

In another series of tests using the lymphocyte-CG procedure of this invention, correlation was found between the percent of lymphocyte cells testing positive for hCG and the effective T-cell concentration. In this series of tests, T-cell concentration was measured in a number of patients by the standard E-Rossette technique. The lymphocyte cells were then treated with VCN, as described, and the T-cell concentration was measured again. The difference between the T-cell concentration by these two tests was found to correlate with the percentage of lymphocyte cells found to contain hCG. That is, the difference between the tests for T-cell concentration may be said to be a count of the inactive or inhibited lymphocyte cells. This test is then evidence that hCG inhibits T-cell function in the immunoprotective system of the host.

The diagnostic test of this invention is therefore believed to be the first clinical procedure which can establish the presence or absence of human chorionic gonadotropin in lymphocyte cells. The lymphocyte-hCG test is highly specific and sensitive to the presence of hCG. Where hCG is found in the lymphocyte cells and the patient is not pregnant, cancer is confirmed in the patient's system.

We claim:

1. A diagnostic blood test for human chorionic gonadotropin comprising the steps of:
   (a) separating the white blood cells from the whole blood sample to be tested;
   (b) treating the cells with neuraminidase;
   (c) washing the cells to remove excess neuraminidase;
   (d) treating the cells with antiserum specific to the beta-subunit of human chorionic gonadotropin, said antiserum including a clinically detectable label;
   (e) washing excess antiserum from the cells; and
   (f) clinically determining the presence or absence of said label; the presence of said label indicating the presence of human chorionic gonadotropin in the blood sample tested.

2. The diagnostic test defined in claim 1, wherein neuraminidase is vibro cholerera neuraminidase.

3. The diagnostic blood test defined in claim 1, wherein said label is a radioactive isotope and the presence of the label is determined by counting the radiation of the sample with a radiation counter, providing a quantitative analysis for human chorionic gonadotropin.

4. The diagnostic blood test defined in claim 3, wherein said radioactive isotope is selected from the group consisting of radioiodine 125, radioiodine 131 and tritium.

5. The diagnostic blood test defined in claim 3, wherein said label is conjugated to said antiserum.

6. The diagnostic blood test defined in claim 3, wherein said label is conjugated to a second antiserum specific to said first antiserum.

7. The diagnostic blood test defined in claim 1, wherein said label is fluorescein and the presence of said label and human chorionic gonadotropin is determined by examining said cells under a fluorescent microscope.

8. The diagnostic blood test defined in claim 7, wherein said fluorescein label in conjugated to a second antiserum specific to said first antiserum.

9. A diagnostic test for determining the presence of human chorionic gonadotropin in a blood sample, the presence of human chorionic gonadotropin indicating the presence of cancer, comprising the steps of:
   (a) separating the lymphocytes from the blood sample to be tested;
   (b) treating said lymphocyte cells with a neuraminidase;
   (c) washing said lymphocyte cells to remove excess neuraminidase;
   (d) treating said cells with an antiserum specific to the beta-subunit of human chorionic gonadotropin, said antiserum including a radioactive label;
   (e) washing said lymphocyte cells to remove excess antiserum; and
   (f) determining the presence of human chorionic gonadotropin in the lymphocyte cells by counting the gamma radiation; the presence of human chorionic gonadotropin indicating the presence of cancer where the host is not pregnant.

10. The diagnostic test defined in claim 9 wherein said neuraminidase is vibro cholerera neuraminidase and the concentration of vibro cholerera neuraminidase is about 10 units of vibro cholerera neuraminidase per $10^6$ lymphocyte cells.

11. The diagnostic test defined in claim 9, wherein said radioactive label is selected from the group consisting of radioiodine 125, radioiodine 131 and tritium.

12. The diagnostic test defined in claim 8, wherein said radioactive label is conjugated to said antiserum specific to the beta-subunit of human chorionic gonadotropin.

13. A diagnostic blood test for determining the presence of human chorionic gonadotropin as an indication of cancer, comprising the steps of:
   (a) separating the white blood cells from the whole blood sample;
   (b) treating said cells with neuraminidase;

(c) washing excess neuraminidase from said white blood cells;
(d) treating said white blood cells with a first antiserum specific to the beta-subunit of human chorionic gonadotropin raised in a host animal;
(e) treating said cells with a second antiserum specific to the gamma globulin of said host animal, conjugated to fluorescein;
(f) washing excess antiserum from said white blood cells; and
(g) examining said cells for fluorescence; if fluorescence is found, human chorionic gonadotropin is present in the blood sample tested and if the patient is not pregnant, cancer has been established.

14. The diagnostic test defined in claim 13, wherein said neuraminidase is vibro cholerera neuraminidase and the concentration is about 10 units of neuraminidase to $10^6$ cells.

15. A diagnostic test kit for determining the presence of human chorionic gonadotropin in a blood sample, comprising a neuraminidase and an antiserum specific to the beta-subunit of human chorionic gonadotropin, said antiserum including a clinically detectable label.

16. The diagnostic test kit defined in claim 15 wherein said neuraminidase is vibro cholerera neuraminidase.

17. The diagnostic test kit defined in claim 15, wherein said label is a radioactive label selected from the group consisting of radioiodine 125, radioiodine 131, and tritium.

18. The diagnostic test kit defined in claim 15, wherein said label is fluorescein.

19. The diagnostic test kit defined in claim 15, wherein said antiserum includes two separate constituents, including an antiserum specific to the beta-subunit of human chorionic gonadotropin raised in a host animal and an antiserum specific to the gamma globulin of said host animal conjugated to said label.

* * * * *